United States Patent
Krueger et al.

[11] Patent Number: 5,868,253
[45] Date of Patent: *Feb. 9, 1999

[54] HINGED SUPPORT COLLAR FOR MECHANICAL HEART VALVE PACKAGING

[75] Inventors: Kurt D. Krueger, Stacy; Neil P. Dohm, Inver Grove Heights; Constance L. Roos, Oakdale, all of Minn.

[73] Assignee: St. Jude Medical, Inc., St. Paul, Minn.

[ * ] Notice: The term of this patent shall not extend beyond the expiration date of Pat. No. 5,720,391.

[21] Appl. No.: 939,191

[22] Filed: Sep. 29, 1997

Related U.S. Application Data

[63] Continuation-in-part of Ser. No. 623,687, Mar. 29, 1996, Pat. No. 5,720,391.

[51] Int. Cl.⁶ .................................................. A61B 17/06
[52] U.S. Cl. ..................... 206/438; 206/363; 206/583
[58] Field of Search ................................ 206/363, 438, 206/583, 525; 623/2, 900

[56] References Cited

U.S. PATENT DOCUMENTS

| | | |
|---|---|---|
| 4,011,947 | 3/1977 | Sawyer . |
| 4,101,031 | 7/1978 | Cromie . |
| 4,182,446 | 1/1980 | Penny . |
| 4,211,325 | 7/1980 | Wright . |
| 4,512,471 | 4/1985 | Kaster et al. . |
| 4,542,825 | 9/1985 | Thomas et al. . |
| 4,585,453 | 4/1986 | Martin et al. . |
| 4,679,556 | 7/1987 | Lubock et al. . |
| 4,697,703 | 10/1987 | Will . |
| 4,750,619 | 6/1988 | Cohen et al. . |
| 4,801,015 | 1/1989 | Lubock et al. . |
| 5,148,920 | 9/1992 | Walker . |
| 5,236,450 | 8/1993 | Scott ........................................ 623/2 |
| 5,386,908 | 2/1995 | Sinn . |
| 5,403,305 | 4/1995 | Sauter et al. . |
| 5,405,005 | 4/1995 | White . |
| 5,443,502 | 8/1995 | Caudillo et al. . |
| 5,447,230 | 9/1995 | Gerondale . |
| 5,560,487 | 10/1996 | Starr ...................................... 206/438 |
| 5,720,391 | 2/1998 | Dohm et al. ........................... 206/438 |

Primary Examiner—Bryon P. Gehman
Attorney, Agent, or Firm—Hallie A. Finucane, Esq.; Westman, Champlin & Kelly, P.A.

[57] ABSTRACT

Packaging is provided for a heart valve prosthesis. A holder is adapted to grasp the heart valve prosthesis and includes a post. The packaging includes a collar for holding the post of the holder. An inner tray of the packaging receives the collar such that the prosthesis is suspended within the inner tray. An outer tray receives the inner tray. An inner tray lid seals the inner tray and an outer tray lid seals the outer tray.

18 Claims, 4 Drawing Sheets

5,868,253

HINGED SUPPORT COLLAR FOR MECHANICAL HEART VALVE PACKAGING

This is a Continuation-in-part application of U.S. Ser. No. 08/623,687, filed on Mar. 29, 1996 now U.S. Pat. No. 5,720,391.

FIELD OF THE INVENTION

The present invention relates to packaging and a holder for a heart valve prosthesis. More particularly, the present invention relates to packaging for a heart valve prosthesis.

BACKGROUND OF THE INVENTION

Heart valve prostheses are used to replace the natural heart valve of a patient. One type of heart valve prosthesis is shown in U.S. Pat. No. 4,276,658, issued Jul. 7, 1981, entitled HEART VALVE PROSTHESIS. Following manufacture and prior to implantation, the prosthesis must be transported in a sterile, sealed package. The package should be designed so that it is easily disassembled for removal of the valve during surgery yet provides a secure, sterile and protective container during transportation.

Various packaging designs are shown in the prior art. For example, U.S. Pat. No. 4,101,031, issued Jul. 18, 1978 to Cromie, entitled "PACKAGE FOR PROSTHETIC HEART VALVE OR THE LIKE" shows a rigid canister which screws together and includes an O-ring. U.S. Pat. No. 4,512,471, issued Apr. 23, 1985 to Kaster et al., entitled "STORAGE UNIT" also shows a canister which screws together. The Cohen et al. reference, U.S. Pat. No. 4,750,619, issued Jun. 4, 1988, entitled "PACKAGE WITH TRAY FOR SECURING AND PRESENTING A STERILE PROSTHETIC IMPLANT ELEMENT" shows three containers which sit within each other. The Lubock et al. reference, U.S. Pat. No. 4,801,015, issued Jan. 31, 1989 entitled "RELEASABLE HOLDER AND PACKAGE ASSEMBLY FOR A PROSTHETIC HEART VALVE" also shows a rigid container which screws together.

The heart valve prosthesis is typically suspended in the package by a holder. One such holder is described as a hanger in U.S. Pat. No. 5,443,502, issued Aug. 22, 1995 to Caudillo et al., entitled ROTATABLE HEART VALVE HOLDER. The holder should be constructed such that it may be held in the packaging.

SUMMARY OF THE INVENTION

The present invention provides packaging for a heart valve prosthesis. The packaging provides a sterile, sealed container for the heart valve prosthesis following manufacture and prior to implantation. The packaging includes a tray having a recess formed therein. A heart valve prosthesis holder is adapted to carry the heart valve prosthesis. A collar is shaped to fit into the inner tray and includes a hinge which pivotably couples a first jaw to a second jaw which is moveable between an open position and a closed position. The first and second jaws are shaped to clamp about the heart valve prosthesis holder when in the closed position to suspend the heart valve prosthesis in the tray. In another aspect of the invention, the collar includes a plurality of legs which are adapted to couple to leg receptacles in the tray.

DETAILED DESCRIPTION OF THE PREFERRED EMBODIMENTS

Figure 1:
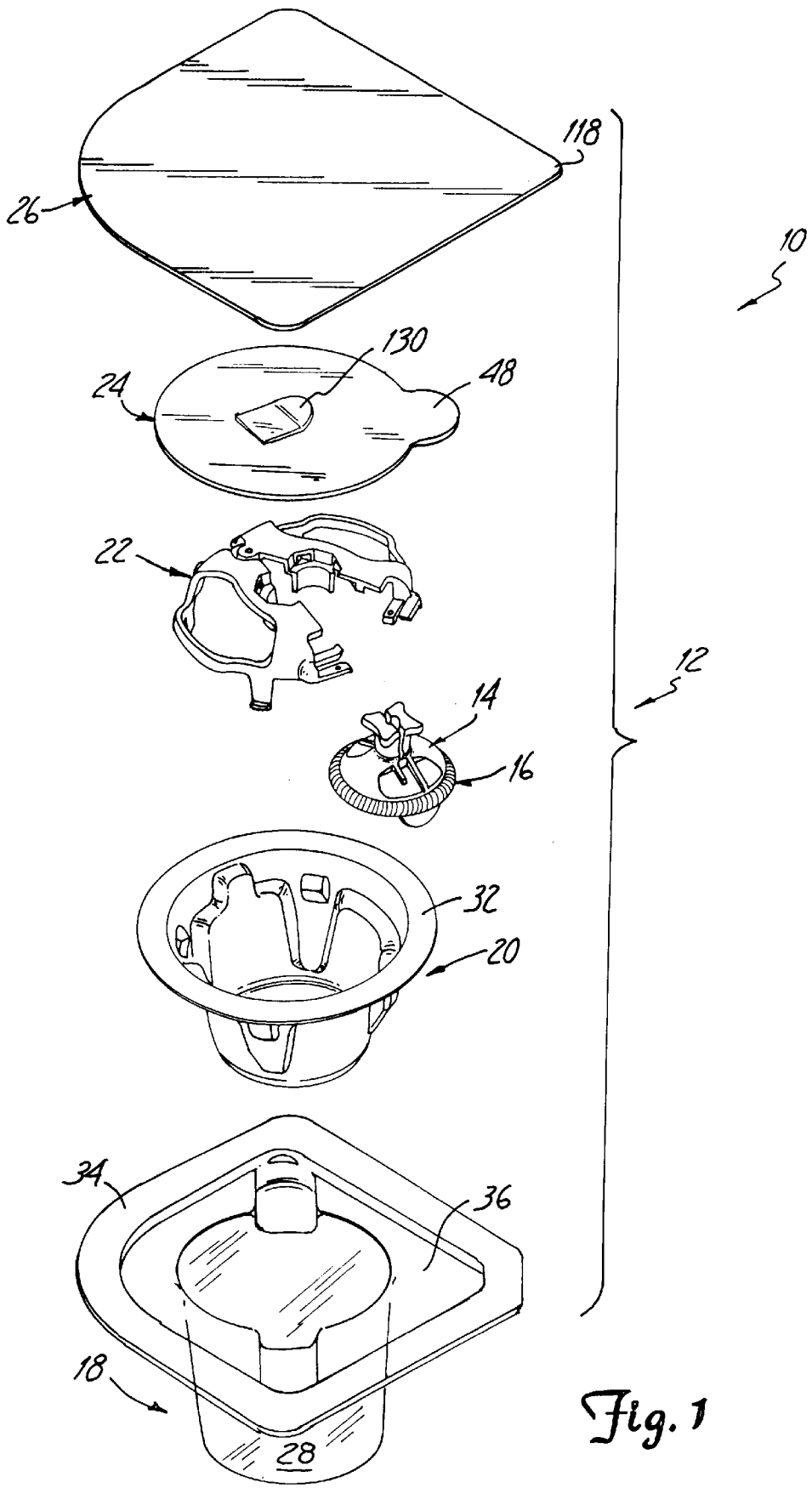
FIG. 1 is an exploded perspective view of the packaging in accordance with the present invention.

FIG. 1 is an exploded top perspective view of assembly 10 in accordance with the present invention. Assembly 10 includes packaging 12, valve holder 14 and heart valve prosthesis 16. Packaging 12 includes outer tray 18, inner tray 20, collar 22, inner tray lid 24 and outer tray lid 26.

As shown in FIG. 1, inner tray 20 fits into cavity or recess 28 of outer tray 18. Similarly, collar 22, heart valve prosthesis 16 and valve holder 14 fit in cavity or recess 30 of inner tray 20. Inner tray lid 24 fits over inner tray 20 and seals to inner tray sealing flange 32. Similarly, outer tray lid 26 fits over outer tray 18 and inner tray 20 and seals to outer tray sealing flange 34. Inner tray sealing flange 32 rests on flange shoulder 36 of outer tray 18 thereby supporting inner tray 20.

Figure 2:
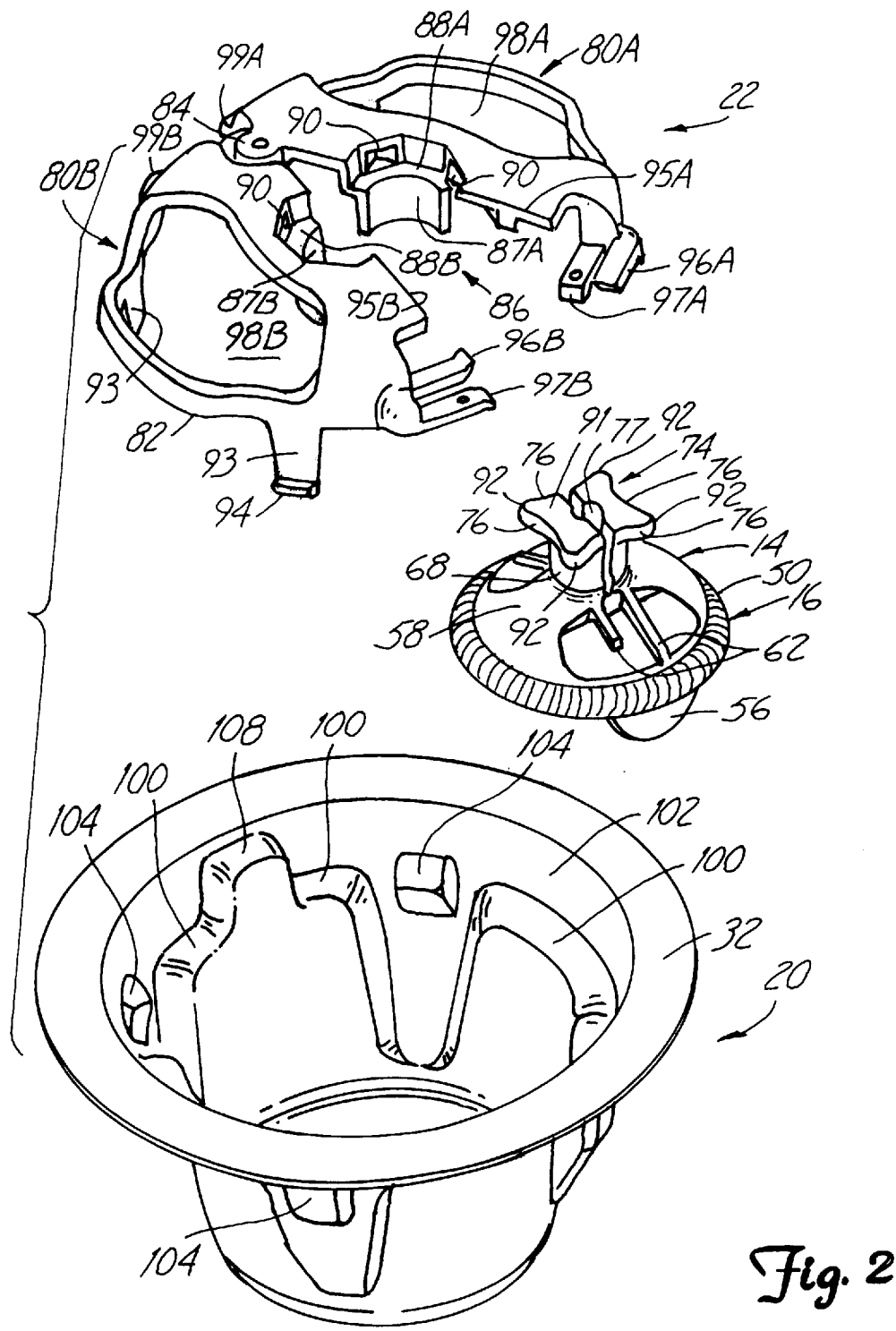
FIG. 2 is an exploded perspective view of a collar and inner tray in accordance with the present invention and a heart valve prosthesis attached to the holder.

FIGS. 2 through 6 describe the preferred embodiment and show how individual pieces fit together and advantageously cooperate. FIG. 2 is an exploded view of valve holder 14, collar 22 and inner tray 20. Prosthesis 16 includes suture cuff 50, prosthesis body 52 (not shown in FIG. 2) and an occluder(s) or leaflet(s) carried therein (not shown). The occluder is supported by pivot guards 56. Valve holder 14 includes body 58 and holder post 68. Post 68 includes post head 74 having multiple circumferentially spaced finger recesses or grips 76 and provides a generally square shape. In one embodiment (not shown) only two opposed grips 76 are provided. Other shapes are within the scope of the present invention. A receptacle 77 extends through the axis of post 68 and is adapted to receive the tip of an elongated handle (not shown). Ridges 62 are adapted to receive a suture therethrough which is used to secure valve 16 to holder 14.

Figure 3:
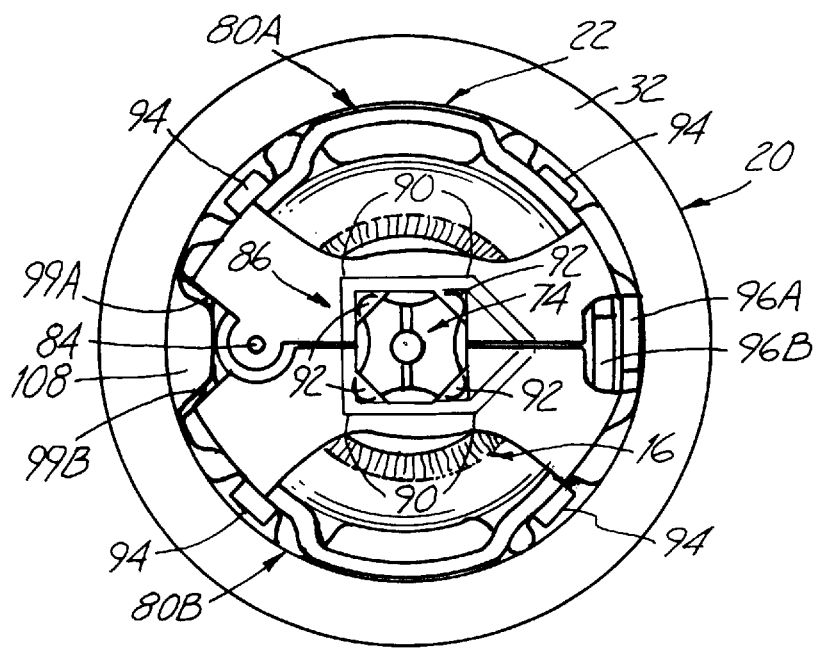
FIG. 3 is a top plan view and FIG. 4 is a side elevational view of an inner tray and collar used in packaging in accordance with the invention shown in an assembled condition.

Collar 22 includes a first top jaw 80A and a second jaw 80B movably attached to jaw 80A at pivot 84 to move between an open position (shown in FIG. 2) and a closed position (shown in FIG. 3). Holder post 68 fits into post clamp 86 formed in the center of collar 22. Walls 87A and 87B of post clamp 86 are configured to conform around post 68. Post clamp 86 also includes post head support surfaces 88A and 88B and tip receiving recesses 90. Tips 92 of post clamp 86 prevent rotational and axial motion of post with respect to collar 22, which also prevents top 91 of post head 74 from coming in contact with lid 24. Post head support surfaces 88A and 88B are recessed from jaws 80A and 80B and are positioned and shaped to support holder post head 74. Recesses 90A, 90B interface with post tips 92 to prevent rotation and prevent post head 74 from contacting inner tray lid 24. Collar 22 includes leg extensions 93 each having locking tips 94 positioned at their distal ends. Leg extensions 93 and locking tips 94 are used for locking collar 22 into inner tray 20, as explained below. Jaws 80A, 80B each include abutting surfaces 95A and 95B positioned opposite pivot 84 which are in abutting contact when jaws 80A and 80B are in the closed position. Additionally, jaws 80A and 80B include upper locking members 96A and 96B and lower locking members 97A and 97B, respectively, positioned opposite pivot 84. Locking members 96A,B and 97A,B are adapted to grasp and lock on opposing locking members when jaws 80A and 80B are in the closed position thereby releasably securing jaws 80A and 80B in the closed position. Each jaw 80A and 80B also includes a cut away region 98A and 98B formed therein which may be grasped by surgical personnel and which allows for circulation of sterilization gases and for visibility of the product. Rear abutting surfaces 99A and 99B are positioned adjacent pivot 84 for abutting contact when jaws 80A and 80B are in a fully open position. Additionally, rear abutting surfaces 99A, 99B form a gap between them when jaws 80A and 80B are in the closed position. The gap interfaces with protrusion 108 formed on the inner rim of inner tray 20. The interface prevents collar 22 from rotating with respect to inner tray 20.

Inner tray 20 includes collar support surfaces or ledges 100. Collar support surfaces 100 are generally flat, circumferentially interspersed and extend radially inward from wall 102 which forms a shelf for placement of lip 82 of collar 22. Shelf 100 supports collar at 82A,82B, 99A,99B and 97A, 97B (four approximately equally spaced points for stability). Collar lock protrusions 104 extend radially inward to create bumps protruding from wall 102, are circumferentially interspersed, and are positioned near the plane created by support ledges 100. Collar lock protrusions 104 alternate between adjacent collar support surfaces 100. Inner tray 20 also includes middle ledge 108 positioned to fit between rear abutting surfaces 99A, 99B when jaws 80A and 80B are in the closed position. Additionally, ledge 108 prevents rotation of collar 22 in tray 20.

Figure 4:
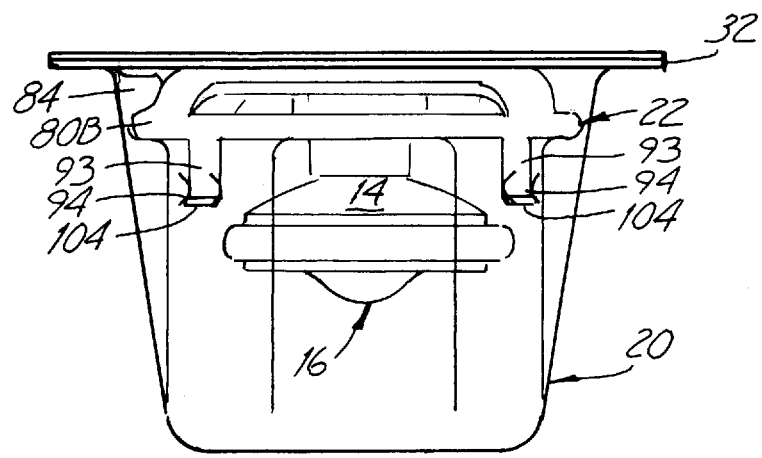

FIG. 3 is a top plan view and FIG. 4 is a side elevational view of assembly holder 14, valve 16, collar 22 and inner tray 20 in an assembled condition. As shown in the figures, heart valve prosthesis 16 is securely held by valve holder 14, and valve holder 14 is suspended in inner tray 20. Valve holder 14 is carried in collar 22 at post clamp 86 and on post head support surface 88, shown in FIG. 2. Recesses 90 prevent rotation of valve holder 14 by securing post head tips 92.

Collar 22 is secured in inner tray 20 by leg extensions 93 and locking tips 94 which fit in collar lock protrusions 104. Rotation of collar 22 within tray 20 is prevented by rear abutting surfaces 99A, 99B which abut ledge 108 of tray 20. Inner tray 20 is sealed by inner tray lid 24 shown in FIG. 1.

Figure 5:
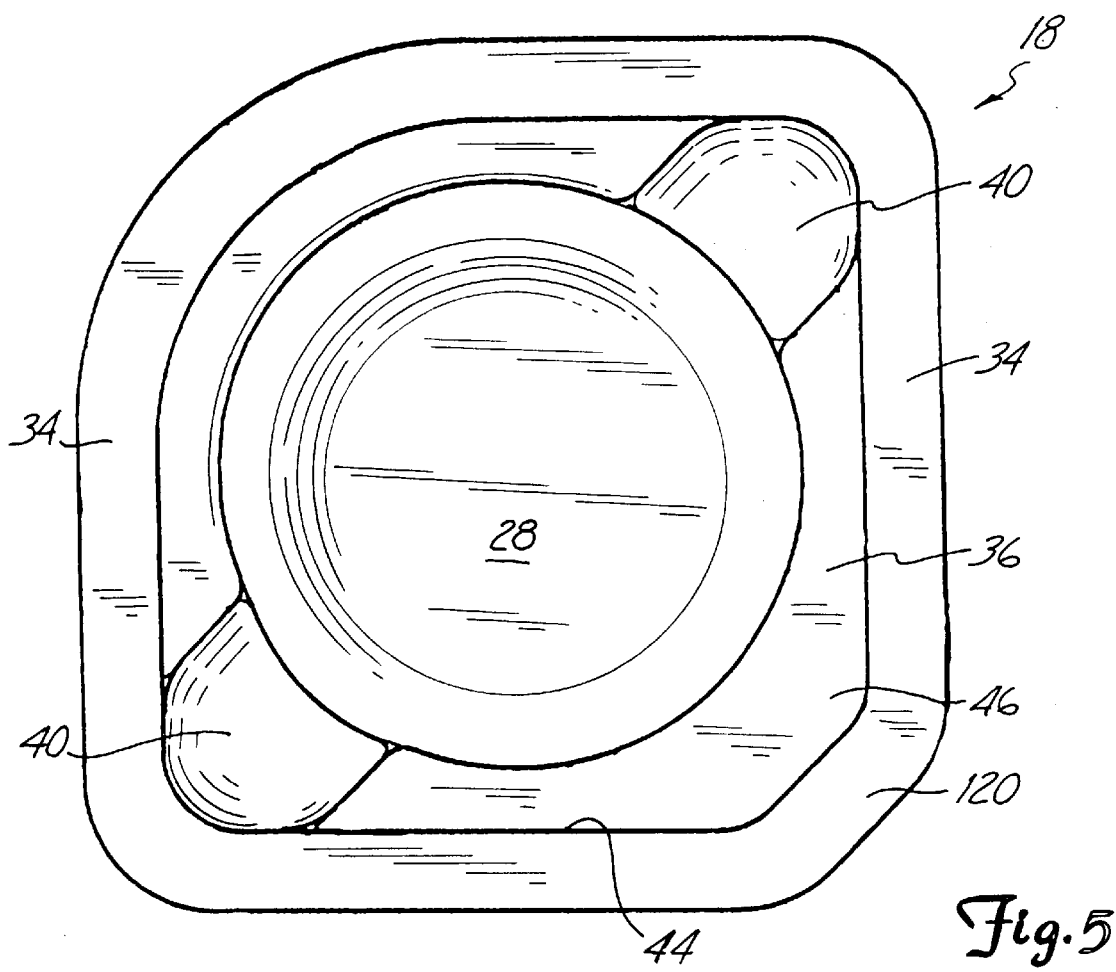
FIG. 5 is a top plan view and FIG. 6 is a side elevational view of an outer tray in accordance with the present invention.
Figure 6:
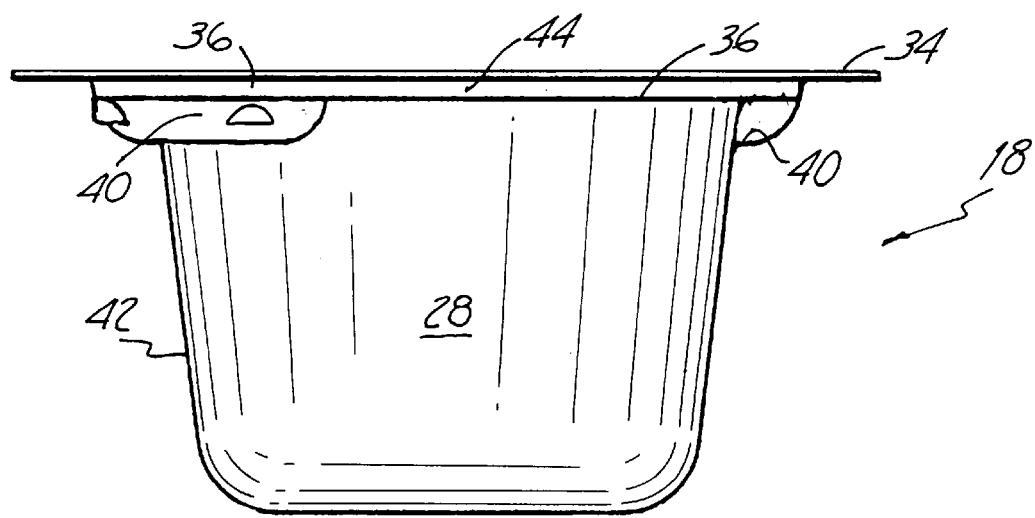

FIG. 5 is a top plan view and FIG. 6 is a side elevational view of outer tray 18. Outer tray 18 includes finger recesses 40 formed in flange shoulder 36 on opposite sides of cavity or recess 28. Recess 28 is formed by wall 42. Finger recesses 40 extend downward from shoulder 36 to provide means for removal of inner tray 20 (shown in FIG. 1), from cavity 28. Finger recesses 40 also provide a passageway for sterilization gases to penetrate into cavity 28 when inner tray 20 is nested in place. The depression formed by flange shoulder 36 forms lip inner wall 44 which extends between sealing flange 34 and flange shoulder 36. A portion of flange shoulder 36 forms tab receiving shoulder 46 for receiving tab 48 of inner lid 24 (shown in FIG. 1). Flange shoulder 36 is shaped to support flange 32 of inner tray 20. With inner lid 24 sealed to flange 32, tab 48 fits in tab receiving shoulder 46 (shown in FIG. 1). Further, outer tray lid 26 seals to sealing flange 34 and tab 118 extends over cut-away portion 120 of sealing flange 34 providing a gripping surface on outer lid for easy removal, as shown in FIG. 1. In one embodiment, lids 24 and 26 are heat sealed using a platen during manufacture.

Inner tray 20 fits in outer tray 18 and is positioned such that tab 48 lies over tab receiving shoulder 46. Outer tray lid 26 seals outer tray 18 and maintains assembly 10 together during shipping.

During surgery, prosthesis 16 is removed in accordance with the following steps. Outer tray lid 26 is removed by pulling on tab 118 which overhangs portion 120 of sealing flange 34. This exposes inner tray lid 24. Inner tray 20 is removed by placing, for example, a thumb and forefinger in finger recesses 40 such that sealing flange 32 of tray 20 is grasped without breaking the sterile barrier. Alternatively, outer tray 18 can be tipped from inner tray 20. Furthermore, a tab 130 shown in FIG. 1 can be attached to lid 24 such that the surgical personnel can grasp tab 130 and lift inner container 20 from outer container 18. Inner tray 20 is then withdrawn from outer tray 18 and outer tray 18 is discarded. Inner tray lid 24 is removed by pulling on tab 48 which extends over flange 32. This exposes post head 74. An elongated handle (not shown) may be inserted into receptacle 77 while grasping tray 20. The convex shape of the top of collar 22 tends to distribute a downward force in an outward, radial direction such that a force may be applied while inserting the handle into receptacle 77, without causing the collar 22 to collapse. Torsional load may also be applied to receptacle 77 such as that which would be applied if the receptacle were threaded. As described above, rotation of post 68 is prevented by rotation stop walls 90 which lock post 68 in place and by middle ledge 108 and rear abutting surfaces 99A, 99B which prevent rotation of collar 22 within tray 20. After the handle is secured to valve holder 14, collar 22 and valve holder 14 may be pulled out of inner tray 20. This snap removal occurs because the tray and collar are preferably made of a polymeric material which allows for moderate deformation.

Removal of collar 22 from inner tray 20 releases the constraint on shelf placement lip 82 of collar 22 and allows for easy removal of valve holder 14 in the surgical setting. Valve holder 14 is removed from collar 22 by opening jaws 80A and 80B as shown in FIG. 2. Prosthesis 16 is removed from valve holder 14 by cutting a suture (not shown).

During implantation, a surgical personnel may use finger recesses 76 of post head 74 to grasp valve holder 14 and thereby rotate valve body 52. For example, valve body 52 may rotate within suture cuff 50 after suture cuff 50 is attached to the heart tissue annulus. Typically, a surgical personnel will hold finger recesses 76 between a thumb and opposing forefinger.

In a preferred embodiment, trays 18 and 20 and collar 22 are made of a thermally formed polymer, such as polycarbonate which is clear and which may be steam sterilized. In a preferred embodiment, trays 18 and 20 are formed by thermoform molding techniques. Collar 22 is formed by injecting molding. Lids 24 and 26 are preferably made from a porous, steam penetrable spun bonded polyolefin material having sterile barrier properties, such as Tyvek® 1073B available from Dupont de Nemours having an adhesive coating. This allows the assembly 10 to be sterilized while in an assembled condition by forcing sterilization gases through lids 24 and 26 and across surfaces of the interior of trays 18 and 20 and prosthesis 16. Other polymers may be used which better withstand other sterilization techniques such as ethylene oxide gas or gamma radiation. General manufacture and usage would remain unchanged from the steps outlined herein. The finger recesses 40 allows pressure to equilibrate between inner tray 20 and outer tray 18 during vacuum sterilization cycles.

The packaging is advantageous because the prosthesis 16 is suspended within the packaging and does not contact the sides of the packaging. Further, the packaging is easily disassembled during surgery because the trays are not locked together. Using a clear packaging provides visibility which allows easy identification of the product. The flexible nature of the tray containers is advantageous because the lips of the containers allow some limited bending of the Bpackaging when a vacuum is applied to the containers during the sterilization process. The locking nature of the components is useful because a rotational torque can be applied without causing the components to slip within each other. The particular packaging is also well suited for low cost, reliable and easy manufacture and provides reduced costs over prior art packaging. The packaging is designed to withstand vacuum steam sterilization, and the pressure differentials imposed during the steam sterilization cycle. In addition, the packaging of the present invention provides dual sterile barriers in a recyclable container. Further, the packaging does not require additional external shock absorbing material such as open or closed cell foam which allows overall package size reduction.

In the present invention, the product is suspended in the inner tray using a locking mechanism which is held in a closed position by the inner tray. The configuration of the collar and the inner tray prevent upward or downward rotative movement of the collar. The locking mechanism which is utilized to suspend the product within the package functions without any input from the outer tray. This allows the outer tray to function as a shock absorber without effecting the contained product. The design is robust and well suited for transportation and storage. The ability to open the package and present it to the sterile field without breaking the sterile field is considerably easier than in prior art techniques due to the finger recess in the outer package and the fact that the inner tray is not "locked" within the outer tray.

Although the present invention has been described with reference to preferred embodiments, workers skilled in the art will recognize that changes may be made in form and detail without departing from the spirit and scope of the invention. For example, the holder may be of any desired shape to fit within the collar. Furthermore, other post head configurations may be used in which rotation of the post is prevented. Additionally, other types of heart valves and holders and heart valve prostheses of any design from any manufacturer other than those specifically shown may also be used with the present invention. Holder 14 and prosthesis 16 are provided as example configurations. Further, the specific locking members 96A,B and 97A,B are one preferred embodiment of a locking mechanism which is used to releasably secure the jaws in a closed position. However, any other type or configuration of a locking mechanism may be employed. Similarly, any type of hinge mechanism may be used to couple the two jaws together.

What is claimed is:

1. An apparatus for carrying a heart valve prosthesis, comprising:
   a tray having a recess formed therein;
   a heart valve prosthesis holder adapted to carry the heart valve prosthesis; and
   a collar shaped to fit in the tray and having a hinge pivotably coupling a first jaw to a second jaw moveable between an open position and a closed position, the first and second jaws shaped to clamp the heart valve prosthesis holder therebetween when in the closed position to thereby suspend the heart valve prosthesis in the tray.

2. The apparatus of claim 1 wherein the collar includes a plurality of leg extensions adapted to couple to leg receptacles in the tray whereby the prosthesis is suspended in the tray by the collar.

3. The apparatus of claim 1 including a lock mechanism coupled to the collar adapted to lock the collar in the closed position.

4. The apparatus of claim 1 wherein the locking mechanism includes a first locking member extending from the first jaw and a second locking member extending from the second jaw, the first and second locking members positioned for abutting contact when the first and second jaws are in the closed position.

5. The apparatus of claim 1 wherein the heart valve prosthesis holder includes at least one radially extending tip and the collar includes a recess formed therein for receiving the at least one radially extending tip to thereby prevent rotation the holder relative to the collar when the holder is positioned in the collar and the first and second jaws are in the closed position.

6. The apparatus of claim 1 wherein the first and second jaws include first and second abutting surfaces, respectively, positioned to be in abutting contact when the first and second jaws are in the open position.

7. The apparatus of claim 1 including an outer container adapted to receive the tray therein.

8. The apparatus of claim 1 including a lid sealed to the tray to seal the heart valve prosthesis therein.

9. The apparatus of claim 1 wherein the tray includes a protrusion formed therein adapted to engage the collar and thereby prevent rotation of the collar relative to the tray.

10. An apparatus for carrying a heart valve prosthesis, comprising:
    a tray having a recess and leg receptacles formed therein;
    a heart valve prosthesis holder adapted to carry the heart valve prosthesis; and
    a collar adapted to couple to the heart valve prosthesis holder, the collar including a plurality of leg extensions adapted to couple to the leg receptacles in the tray whereby the prosthesis is suspended in the tray by the collar;
    a hinge pivotally coupling a first jaw to a second jaw which are moveable between an open position and a closed position, the first and second jaws adapted to clamp the heart valve prosthesis holder therebetween when in the closed position to thereby suspend the heart valve prosthesis in the tray.

11. The apparatus of claim 10 wherein the collar includes a locking mechanism for releasably locking the collar in the closed position.

12. The apparatus of claim 11 wherein the locking mechanism comprises a first locking member extending from the first jaw and a second locking member extending from the second jaw and positioned to be abutting contact when the first and second jaws are in the closed position.

13. The apparatus of claim 10 wherein the collar includes first and second abutting surfaces on the first and second respective jaws, the first and second abutting surfaces positioned to be in abutting contact when the collar is in the open position.

14. The apparatus of claim 10 wherein the holder includes at least one extending tip and the collar includes a recess for receiving the at least one extending tip therein to thereby prevent rotation of the holder relative to the collar when the holder is coupled to the collar.

15. The apparatus of claim 10 including a container adapted to receive the tray therein.

16. The apparatus of claim 10 including a lid attached to the tray to thereby seal the heart valve prosthesis therein.

17. The apparatus of claim 10 wherein the leg receptacles comprise a plurality of protrusions formed in a wall of the tray and each of the plurality of leg extensions include a tip adapted to fit against the plurality of protrusions.

18. The apparatus of claim 10 wherein the tray includes a protrusion formed therein adapted to engage the collar and thereby prevent rotation of the collar relative to the tray.

* * * * *